United States Patent
Adler et al.

(10) Patent No.: US 9,271,797 B2
(45) Date of Patent: Mar. 1, 2016

(54) ROBOTIC SURGERY

(71) Applicant: GYRUS ACMI, INC., Southborough, MA (US)

(72) Inventors: Doron Adler, Haifa (IL); Shai Finkman, Haifa (IL)

(73) Assignee: Gyrus ACMI, Inc., Southborough, MA (US)

(*) Notice: Subject to any disclaimer, the term of this patent is extended or adjusted under 35 U.S.C. 154(b) by 197 days.

(21) Appl. No.: 13/933,144

(22) Filed: Jul. 2, 2013

(65) Prior Publication Data

US 2015/0012010 A1 Jan. 8, 2015

(51) Int. Cl.
- *A61B 17/00* (2006.01)
- *A61B 19/00* (2006.01)
- *A61B 17/29* (2006.01)

(52) U.S. Cl.
CPC ......... *A61B 19/2203* (2013.01); *A61B 19/5225* (2013.01); *A61B 19/56* (2013.01); *A61B 2017/0046* (2013.01); *A61B 2017/00212* (2013.01); *A61B 2017/00221* (2013.01); *A61B 2017/00477* (2013.01); *A61B 2017/291* (2013.01); *A61B 2019/223* (2013.01); *A61B 2019/2223* (2013.01); *A61B 2019/2269* (2013.01); *A61B 2019/5229* (2013.01)

(58) Field of Classification Search
CPC ............... A61B 19/22; A61B 19/2203; A61B 2017/00221; A61B 19/5225; A61B 2017/00212; A61B 2017/291; A61B 17/29; A61B 2017/0046; A61B 2019/2223; A61B 2017/00477; A61B 2019/2269; A61B 19/56; A61B 2019/5229

USPC ........................................................ 606/1, 130
See application file for complete search history.

(56) References Cited

U.S. PATENT DOCUMENTS

| | | | |
|---|---|---|---|
| 6,558,407 B1 * | 5/2003 | Ivanko et al. | 606/201 |
| 2002/0120252 A1 | 8/2002 | Brock et al. | |
| 2002/0128552 A1 | 9/2002 | Nowlin et al. | |
| 2003/0060808 A1 * | 3/2003 | Wilk | 606/1 |
| 2004/0044279 A1 * | 3/2004 | Lewin et al. | 600/407 |
| 2004/0267089 A1 * | 12/2004 | Otsuka et al. | 600/102 |
| 2006/0116667 A1 * | 6/2006 | Hamel et al. | 606/1 |

(Continued)

FOREIGN PATENT DOCUMENTS

WO 2007038998 A1 4/2007

OTHER PUBLICATIONS

International Application PCT/US14/33903 Search Report dated Sep. 17, 2014.

(Continued)

*Primary Examiner* — Richard Louis
(74) *Attorney, Agent, or Firm* — D. Kligler I.P. Services Ltd.

(57) ABSTRACT

A robotic tool holder, including a housing, configured to be gripped by a human hand, and a wireless transmitter, located within the housing. The holder further includes a plurality of individual controls attached to the housing, the controls being configured, in a first mode of operation of the robotic tool holder, to activate respective motions of a first surgical tool physically attached to the housing in response to manipulation of the controls by the human hand, and in a second mode of operation of the robotic tool holder, to activate via the wireless transmitter respective motions of a second surgical tool remote from and disconnected from the housing in response to the manipulation.

14 Claims, 5 Drawing Sheets

(56) References Cited

U.S. PATENT DOCUMENTS

| | | |
|---|---|---|
| 2006/0201130 A1 | 9/2006 | Danitz |
| 2007/0095355 A1 | 5/2007 | Oomori et al. |
| 2007/0137372 A1 | 6/2007 | Devengenzo et al. |
| 2007/0282371 A1* | 12/2007 | Lee et al. ............... 606/205 |
| 2008/0167522 A1 | 7/2008 | Giordano et al. |
| 2008/0167736 A1 | 7/2008 | Swayze et al. |
| 2008/0188870 A1* | 8/2008 | Andre et al. ............. 606/130 |
| 2011/0112517 A1* | 5/2011 | Peine et al. ............... 606/1 |
| 2011/0295270 A1 | 12/2011 | Giordano et al. |
| 2012/0116391 A1* | 5/2012 | Houser et al. ............. 606/41 |
| 2013/0041292 A1* | 2/2013 | Cunningham ............... 601/2 |
| 2014/0005682 A1 | 1/2014 | Worrell et al. |
| 2014/0316433 A1 | 10/2014 | Navve et al. |
| 2015/0272572 A1 | 10/2015 | Overmyer et al. |

OTHER PUBLICATIONS

International Application PCT/US14/43060 Search report dated Sep. 30, 2014.

U.S. Appl. No. 14/251,605 Office Action dated Jul. 30, 2015.

* cited by examiner

ROBOTIC SURGERY

FIELD OF THE INVENTION

The present invention relates generally to manipulation of tools used for surgery, and specifically to local and remote manipulation of such tools.

BACKGROUND OF THE INVENTION

Many medical procedures are relatively intricate, requiring substantially simultaneous operation of numbers of complex pieces of equipment. In many cases the simultaneous operation is achieved by having two or even more physicians operating the equipment together, during a single procedure. Having more than one physician operating different pieces of equipment, which may interact with each other, requires a high level of communication between the different physicians in order for the multiple operations to be efficient.

SUMMARY OF THE INVENTION

An embodiment of the present invention provides a robotic tool holder, including:

a housing, configured to be gripped by a human hand;

a wireless transmitter, located within the housing; and a plurality of individual controls attached to the housing, the controls being configured, in a first mode of operation of the robotic tool holder, to activate respective motions of a first surgical tool physically attached to the housing in response to manipulation of the controls by the human hand, and in a second mode of operation of the robotic tool holder, to activate via the wireless transmitter respective motions of a second surgical tool remote from and disconnected from the housing in response to the manipulation.

Typically, the individual controls include a magnification/demagnification regulator having a setting defining a ratio, so that in the first mode of operation the ratio corresponds to a movement of a given control relative to a corresponding movement of the first surgical tool and in the second mode of operation the ratio corresponds to the movement of the given control relative to a corresponding movement of the second surgical tool.

In a disclosed embodiment the controls include a flexible joint attached to the housing, the holder further including a retaining cup attached to the flexible joint, the retaining cup being configured to receive and retain the first surgical tool therein, the flexible joint being configured so that in the first mode of operation a movement of the housing with respect to the flexible joint generates only a corresponding movement of the first surgical tool with respect to the flexible joint, and in the second mode of operation the movement of the housing generates only a motion of the second surgical tool.

In a further disclosed embodiment the holder includes a processing unit and motors mounted within the housing, wherein the processing unit receives signals from the plurality of individual controls, and in response:

in the first mode of operation operates the motors to activate the respective motions of the first surgical tool, and in the second mode of operation causes the wireless transmitter to activate the respective motions of the second surgical tool.

In a yet further disclosed embodiment the holder includes a clamping system wherein is mounted the second surgical tool, and further includes a processing unit external to the housing configured to receive signals from the wireless transmitter, and in response to operate the clamping system to perform the respective motions of the second surgical tool.

In an alternative embodiment the second surgical tool includes a multiplicity of surgical tools remote from and disconnected from the housing, the controls including a selector configured to select in the second mode of operation a given surgical tool from the multiplicity of surgical tools.

In a further alternative embodiment the robotic tool holder is operated in an operating theater, and the controls include a selector configured to select a facility used in the operating theater.

There is further provided, according to an embodiment of the present invention a method for implementing a robotic tool holder, including:

configuring a housing to be gripped by a human hand;

locating a wireless transmitter within the housing; and attaching a plurality of individual controls to the housing, wherein the controls are configured, in a first mode of operation of the robotic tool holder, to activate respective motions of a first surgical tool physically attached to the housing in response to manipulation of the controls by the human hand, and in a second mode of operation of the robotic tool holder, to activate via the wireless transmitter respective motions of a second surgical tool remote from and disconnected from the housing in response to the manipulation.

The present invention will be more fully understood from the following detailed description of the embodiments thereof, taken together with the drawings in which:

DETAILED DESCRIPTION OF EMBODIMENTS

Overview

A physician performing invasive surgery has many options in terms of the tools or equipment used and needed for the surgery. Many of these surgical tools, herein assumed to include endoscopes, need to be operated substantially simultaneously. For example, in a typical invasive procedure for performing a biopsy of a part of the bladder, an endoscope may be first inserted into the bladder, a biopsy tool for taking the biopsy is then inserted, and the tool is operated to recover the biopsy, the tool operation being viewed by the endoscope. In many cases more than one surgical tool may need to be inserted into the bladder. For example a second tool, such as a retractor, may be required to manipulate a portion of the bladder so that the biopsy can be correctly taken. Typically, where an endoscope is used together with at least one other tool, more than one physician may be required to manipulate the equipment, leading to very expensive surgery.

Embodiments of the present invention provide a single physician with the capability of controlling multiple surgical tools using a single hand-held tool holder, during surgery performed on a patient. One of the controlled tools, a "local" tool, may be physically connected to the tool holder, and one or more other of the controlled tools may be positioned remotely from the tool holder. The physician may manipulate both types of tool, the local tool and the one or more "remote" tools, using controls on the tool holder. Typically the local and remote tools are configured to operate in generally the same manner, but have different physical parameters, such as a different length, a different diameter, and/or different translational/rotational capabilities of the tool distal end.

In addition, as is described in more detail below, the physician may use the single hand-held tool holder to operate and control other equipment that may be required during the surgery, such as a still or video camera, lighting of a procedure being performed, and the orientation of a patient bed.

DETAILED DESCRIPTION

Figure 1:
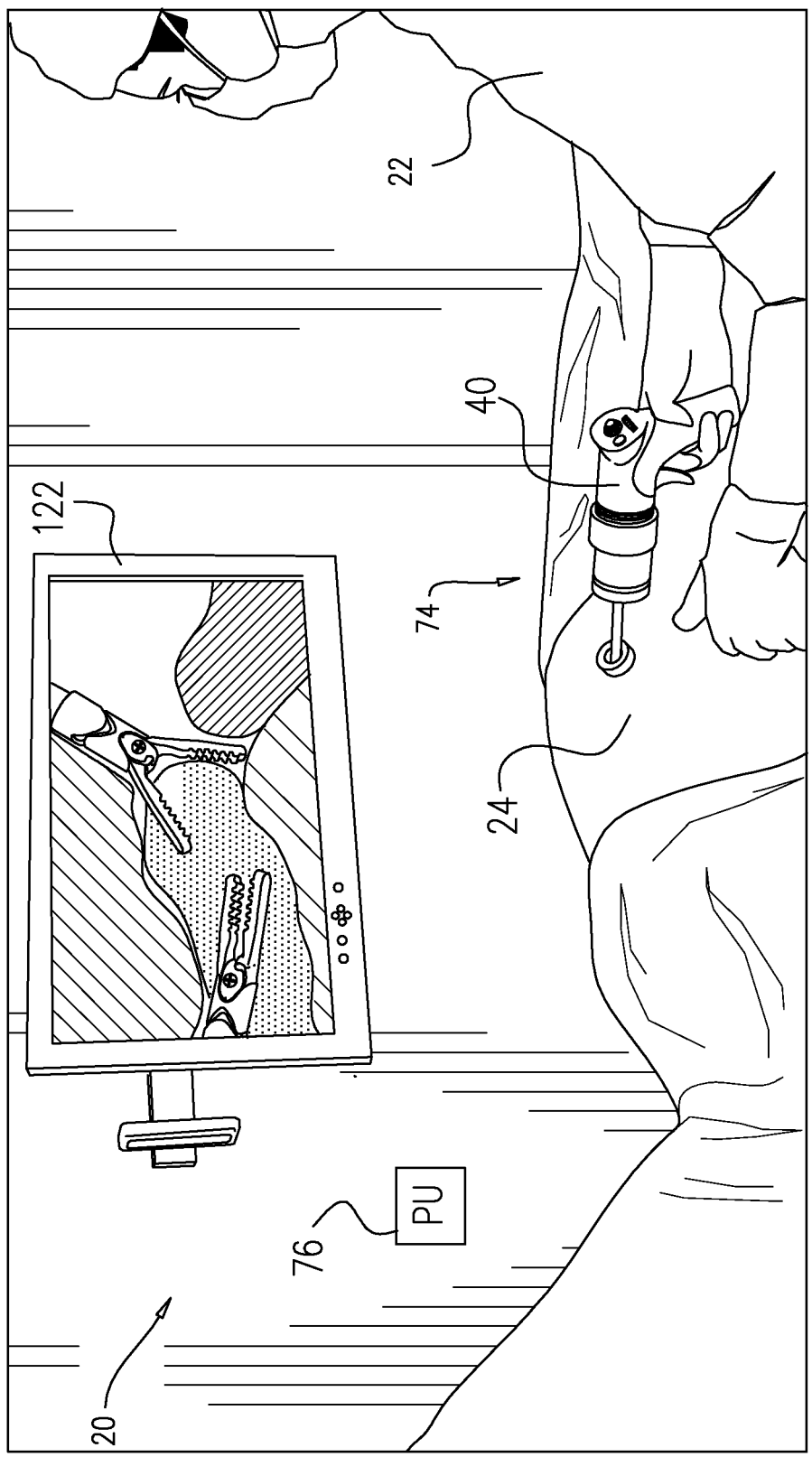
FIG. 1 is a schematic illustration of a robotic surgery system, according to an embodiment of the present invention.

Reference is now made to FIG. 1, which is a schematic illustration of a robotic surgery system 20, according to an embodiment of the present invention. A physician 22 uses system 20 to perform a medical procedure on a patient 24 in an operating theater. System 20 comprises a tool holder 40, which the physician manipulates in order to control actions of tools, such as retraction of tissue, used in the procedure. As is explained in more detail below, the physician may use tool holder 40 to operate "local" surgical tools, i.e., tools which are physically connected to the tool holder. In addition, and as is also explained in more detail below, the physician may also use tool holder 40 to operate "remote" surgical tools, i.e., tools which are physically distant from the tool holder and which have no physical connection with the holder. In order to operate remote surgical tools in this indirect manner, tool holder 40 comprises a wireless transmitter 74 which communicates by wireless transmission with a processing unit (PU) 76. PU 76 operates system 20, typically under overall control of physician 22, the operation of the system including, inter alia, presentation of images of the procedure on a screen 122.

Tool Holder Used to Operate Local Surgical Tool(s)

Figure 2:
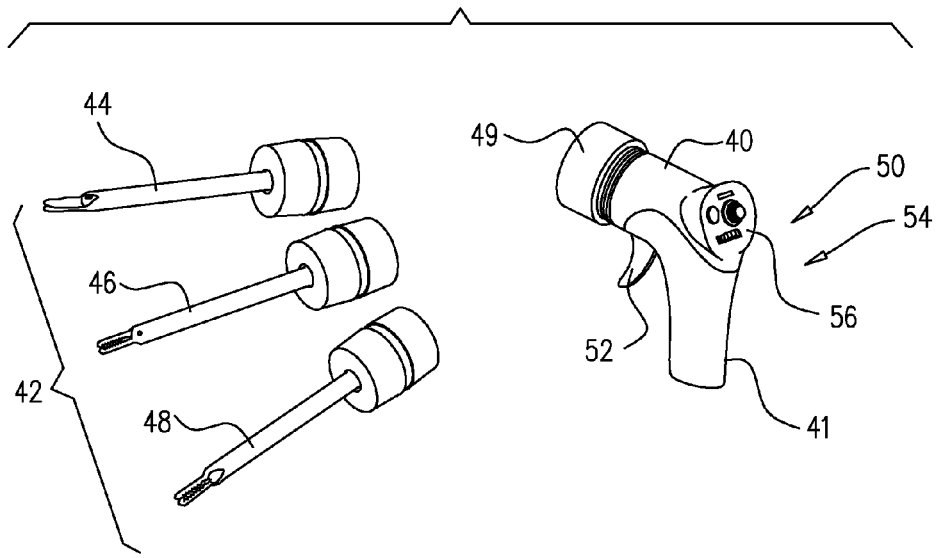
FIG. 2 is a general schematic view of tool holder and of different surgical tools which may be connected to the holder, according to an embodiment of the present invention.
Figure 3:
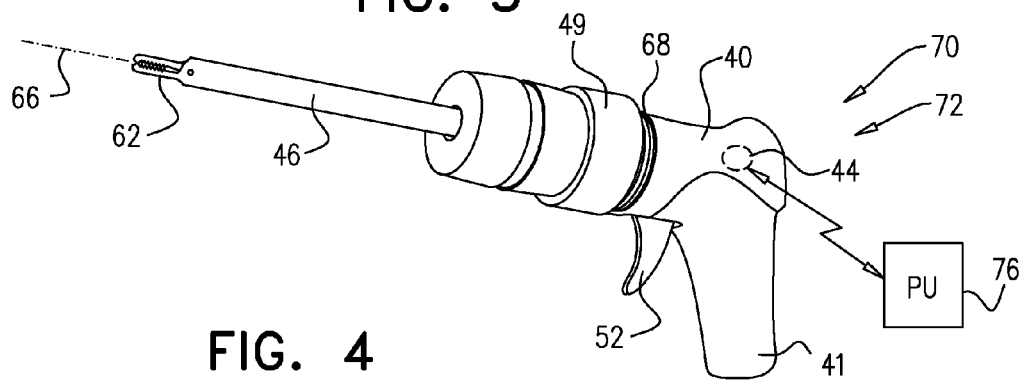
FIG. 3 is a schematic diagram of a specific tool inserted into the tool holder of FIG. 2, according to an embodiment of the present invention.
Figure 4:
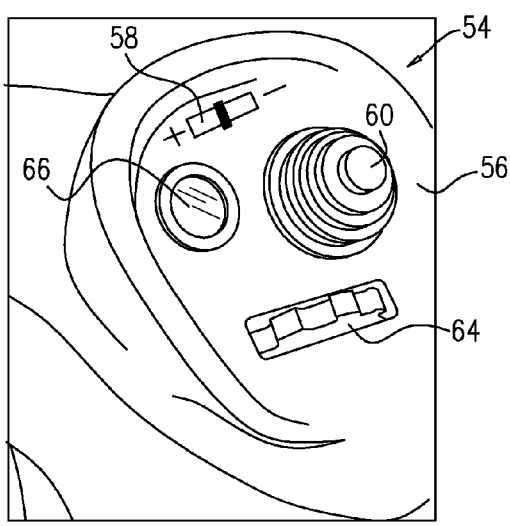

FIG. 2 is a general schematic view of tool holder 40 and of different surgical tools which may be connected to the holder, FIG. 3 is a schematic diagram of a specific tool inserted into the tool holder, and FIG. 4 is a schematic view of controls that are mounted on a portion of the tool holder, according to embodiments of the present invention. Tool holder 40 comprises a housing 41 which is configured to be gripped by a human hand, so that the housing is typically in the form of a pistol grip. The holder connects to any one of a number of different tools 42 (there are three such tools 44, 46, and 48 illustrated by way of example in FIG. 2). Examples of tools 42 include, but are not limited to, a laparoscope, a grasper, a retractor, and a biopsy tool. In the description herein a specific tool 42 may also be referred to as a local surgical tool, a local hand instrument, or just as a hand instrument. FIG. 3 illustrates the insertion of hand instrument 46 into a retaining cup 49 of holder 40. Tool holder 40 comprises a number of controls 50 that regulate the actions of the hand instrument that is connected to the holder. In addition, controls 50 can also be configured to regulate the actions of other tools not physically connected to holder 40, as well as of other equipment used during the surgery. Controls 50 include a trigger 52, proximal controls 54 mounted on a proximal portion 56 of holder 40, and other controls identified in FIG. 3 and described below.

FIG. 4 is a schematic view of controls 54 that are mounted on proximal portion 56. A magnification/demagnification regulator 58, also herein termed a mag/demag regulator, enables the physician operating tool holder 40 to set a ratio of movement of other controls of the holder to the actual motion of the tool connected to the holder. The ratio may typically be set between a value of 4:1 and a value of 1:4, although other ratios are possible. If set to 4:1, movement of a tool is demagnified by a factor of 4 compared to the movement of the control. If set to 1:4, movement of the tool is magnified by a factor of 4.

A joystick button 60 is used to rotate a distal end of the tool in a clockwise or counterclockwise direction around a local axis 63 of the head. A selector 64 enables the physician holding holder 10 to choose other tools or equipment, apart from the tool inserted into the holder, to be operated by the holder. An indicator lamp 66 provides a visual indication to the physician that a particular tool or piece of equipment has been acquired for selection by selector 64. Functions of button 60, selector 64, and lamp 66 are described in more detail below.

Holder 40 has a flexible joint 68 between the distal side of the housing and the retaining cup. Flexible joint 68 is assumed to be included in controls 50. The flexible joint permits relative motion between the housing and the retaining cup. The housing comprises motion detectors 70, which generate signals quantifying the relative motion, the signals being received by a holder processing unit 72. Holder processing unit 72 is typically located within the housing. Holder 40 also comprises wireless transmitter 74 which enables communication between holder 40 and system processing unit (PU) 76, located external to holder 40. The functions of PU 76 are explained with reference FIG. 9.

PU 76 uses software stored in a memory coupled to the processing unit to operate system 20. Results of the operations performed by PU 76 may be presented to physician 22 on screen 122, which typically displays an image of a body cavity of patient 24. The software used by PU 76 may be downloaded to the processor in electronic form, over a network, for example, or it may, alternatively or additionally, be provided and/or stored on non-transitory tangible media, such as magnetic, optical, or electronic memory.

Figure 5:
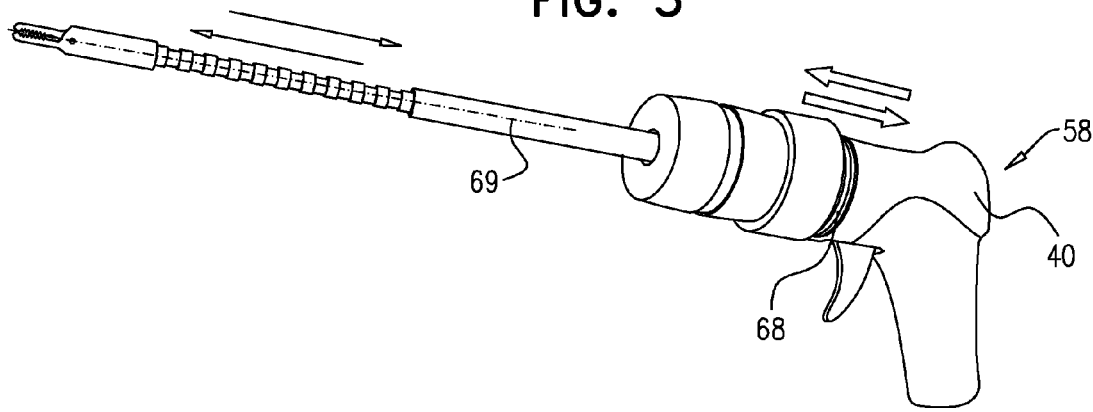
FIGS. 5, 6, 7, and 8 illustrate motions of a hand instrument connected to the tool holder of FIG. 2, according to embodiments of the present invention.

FIGS. 5, 6, 7, and 8 illustrate motions of the hand instrument connected to holder 40 that may be effected by holder 40, according to embodiments of the present invention. FIG. 5 illustrates that by compressing flexible joint 68, the hand instrument extends along a tool axis 69. Similarly, by expanding the flexible joint, the hand instrument retracts along the tool axis. The amount of extension or retraction, for a given compression or expansion of the flexible joint, is set by mag/demag regulator 58.

Figure 6:
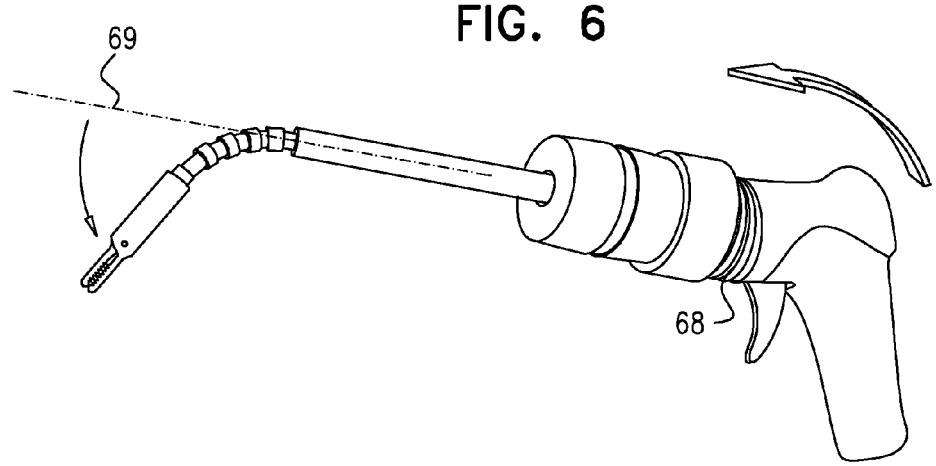
Figure 7:
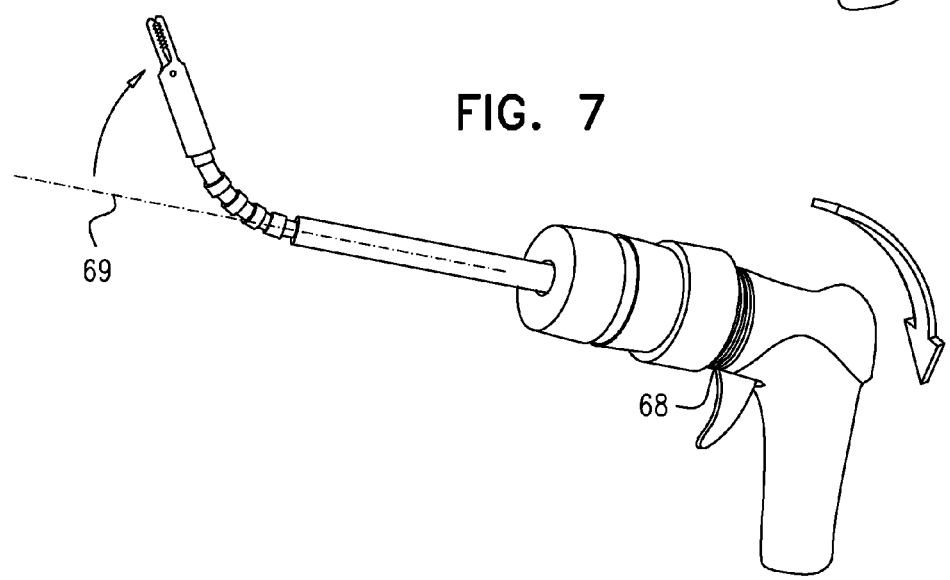

FIGS. 6 and 7 illustrate how the distal end of the hand instrument may be rotated away from axis 69. The distal end rotation is achieved by a corresponding rotation about flexible joint 68. Thus a clockwise/counterclockwise rotation of the housing about joint 68 leads to a corresponding clockwise/counterclockwise rotation of the distal end from axis 69, so that the distal end deflects from axis 69. The plane in which the deflection occurs corresponds to the plane of rotation of joint 68. In other words, for a holder and instrument which are in the plane of the paper, if joint 68 is rotated in the plane of the paper, the distal end deflects in the plane of the paper; alternatively, if joint 68 rotates orthogonal to the plane of the paper, the distal end deflects orthogonal to the plane of the paper.

Figure 8:
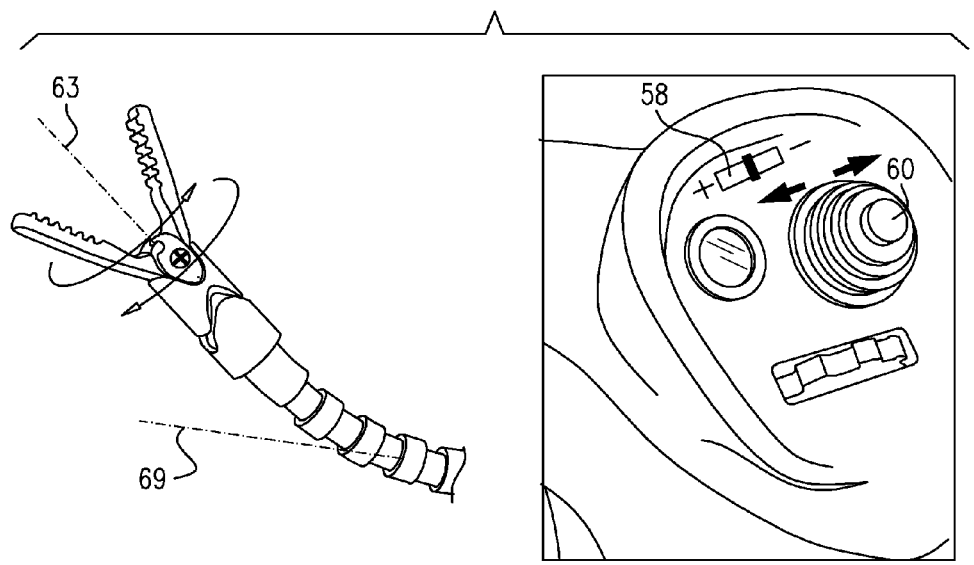

FIG. 8 illustrates, by arrows, how a sideways movement of joystick button 60 effects a rotation of the distal end of the hand instrument about its local axis 63. (In the diagram the local axis is shown as deflected from tool axis 69.) A left movement of button 60 effects a counterclockwise rotation of the distal end; a right movement of the button effects a clockwise rotation of the distal end.

Processor 72 implements the motions described above with respect to FIGS. 5-8 by activating, in response to the signals generated by motion detectors 70, linear and/or rotational motors 74, which are incorporated into the housing. As for the motion described above with reference to FIG. 5, the tool holder operator can set the ratio of the actual motions to the motions of the controls using mag/demag regulator 58.

Figure 9:
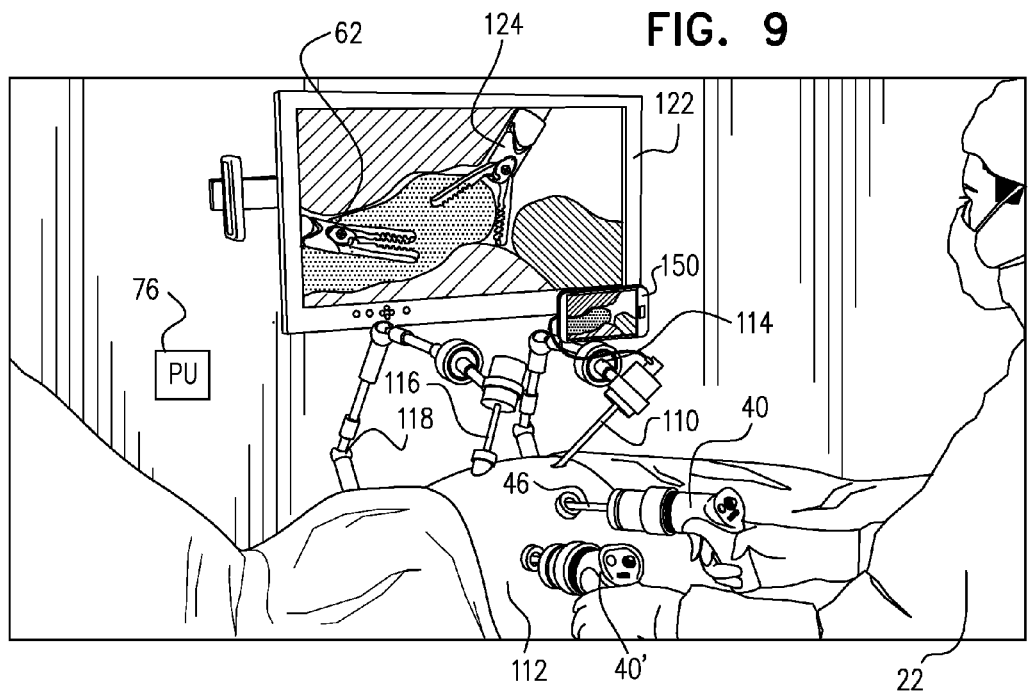
FIG. 9 is a schematic illustration of the use of the tool holder with a hand instrument during a surgical procedure, according to an embodiment of the present invention.

FIG. 9 is a schematic illustration of the use of tool holder 40 with hand instrument 46 during a surgical procedure, according to an embodiment of the present invention. In the procedure, an endoscope 110 has been inserted into the abdomen of patient 24, and is held in place by a clamping system 114 to which it is mounted. An additional tool 116 has also been inserted into the abdomen, and is mounted in a clamping system 118. Tool 116 may be generally similar in function and operation to instrument 46. Both clamping systems are adjustable, having movable joints, and the positions and orientations of endoscope 110 and of tool 116 may be modified using their respective clamping systems. Both clamping systems, and consequently tool 116 and endoscope 110, are remotely controlled, typically via a wireless system, by PU 76. Tool holder 40 is also in communication, typically wireless communication, with processing unit 76.

Endoscope 110 acquires an image of the abdomen, and the image is presented to physician 22 on screen 122. Screen 122 shows distal end 62 of instrument 46, and also shows a distal end 124 of tool 116. An alternative presentation of the image acquired by endoscope 110, such as a central portion of the image on screen 122, may be presented to physician 22 on a screen 150.

As described above, physician 22, while holding tool holder 40 is able to use controls 50 of the holder to adjust distal end 62 of instrument 46. As explained in the following section, the physician is also able to use controls 50 of holder 40 to operate tools or equipment, herein also termed remote instruments, that are remote from the holder. Unlike local hand instrument 46, there is no physical connection between the remote instruments and tool holder 40.

In some embodiments, physician 22 operates a second tool holder 40', which is generally similar in construction and function to tool holder 40. The physician may operate tool holder 40 and tool holder 40' at the same time, the simultaneous operation being achieved by the physician using his/her right hand to operate tool holder 40, and the left hand to operate tool holder 40'. Operation of tool holder 40' enables the physician to operate hand instruments attached to, i.e., local to, holder 40', as well as instruments remote from holder 40'. Hand instruments local and remote from holder 40' are different from hand instruments local and remote from tool holder 40, and It will be understood that by using the two tool holders, single physician 22 may simultaneously manipulate two hand instruments locally, as well as control one, two, or even more hand instruments remotely.

Tool Holder Used to Operate Remote Surgical Tool(s)

Figure 10:
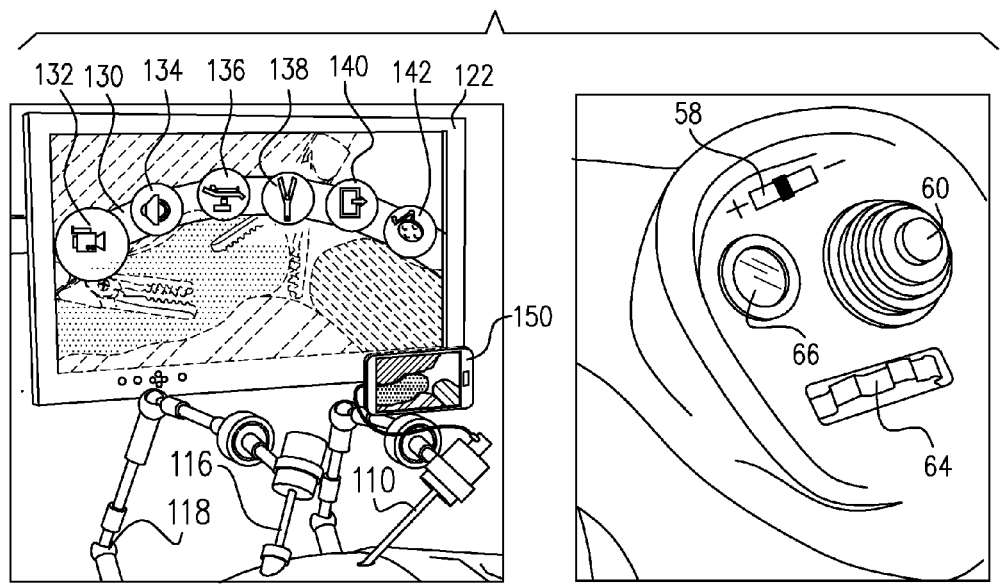
FIG. 10 and FIG. 11 illustrate schematically a process for selecting and operating a remote surgical tool, according to an embodiment of the present invention.
Figure 11:
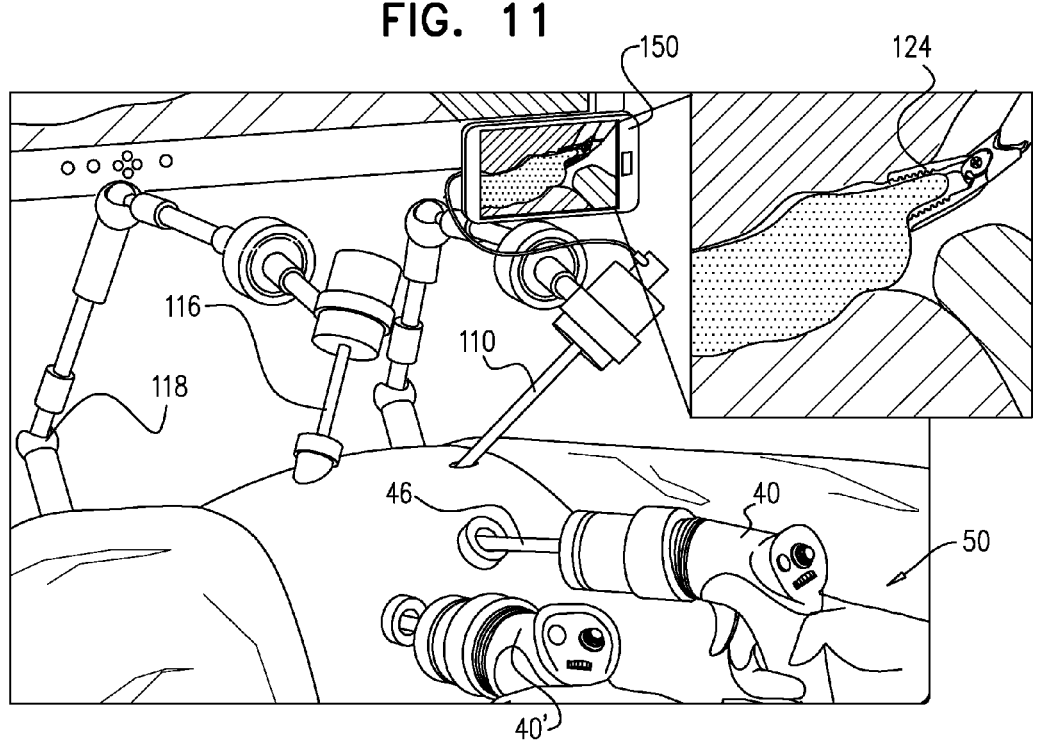

FIG. 10 and FIG. 11 illustrate schematically a process for selecting and operating a remote surgical tool, also herein termed a remote instrument, with tool holder 40, according to an embodiment of the present invention. In order to operate a remote instrument, physician 22 uses PU 76 to call up a selection image 130 on screen 122. The calling up of selection image 130 may be by any convenient method, and herein, by way of example, the physician is assumed to use a foot switch (not shown). The calling up of the selection image automatically disengages controls 50 from local hand instrument 46. However, as shown in FIG. 11, hand instrument 46 remains physically in place and connected to holder 40.

Selection image 130 displays a menu of instruments that the physician may choose from. By way of example, the menu is shown in iconical form in the figure, but it may also comprise text, or other graphics. FIG. 10 gives as examples an imaging icon 132, a music icon 134, a patient bed icon 136, a remote tool icon 138, a return icon 140, and an operating theater illumination icon 142. Imaging icon 132, music icon 134, patient bed icon 136, remote tool icon 138, return icon 140, and operating room illumination icon 142 respectively represent endoscope 110, a control for music, a control for the patient bed (not shown), a control for remote tool 116, a control to return to local operation using holder 40, and a control for the operating room lights (not shown). Selection of music icon 134, patient bed icon 136, or illumination icon 142 allow physician 22 to operate corresponding facilities of the operating theater.

In addition to the foot switch calling up selection image 130 and disengaging controls 50 from hand instrument 46, operation of the foot switch also activates selector 64, herein assumed to be a rotary switch. Rotation of selector 64 sequentially highlights each of the icons of image 130 in turn. To select a particular element represented by an icon, the physician stops rotating the selector, and after a preset time, say of 2 seconds, the highlighted element is automatically selected and indicator light 66 flashes to confirm to the physician that the selection has been implemented.

Once a remote element has been selected, PU 76 accepts signals from controls 50 for operating the selected element, effectively coupling controls 50 to the element.

For example, if selector 64 is used to highlight icon 138, and thus select remote tool 116, the physician is able to use controls 50 on holder 40 to manipulate distal end 114 of tool 116. The manipulation is substantially the same as the manipulation, explained above, for instrument 46.

In the case of other remote surgical tools or elements that may be selected using selector 64, and that are not similar to a local hand instrument, screen 122 may display functions of controls 50 that correspond to the selected tool or instrument, and also indicate which controls (if any) are not functional. For example, if operating room illumination icon 142 is selected, screen 122 may display that joystick 60 may tilt the operating room lights, and that trigger 52 is not functional.

At any time the physician may decouple the remote instrument from controls 50, and recouple the controls to the tool physically connected to holder 40, i.e., to tool 46. The decoupling and recoupling is typically implemented using a similar method as that used for calling up selection image 130. For example, the foot switch referred to above may be configured as toggling between a first state of calling up the selection image and decoupling the tool physically connected to the holder, and a second state of recoupling the connected tool and removing the selection image (if still present) from screen 122. Alternatively or additionally, the decoupling and recoupling may be implemented using return icon 140.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A robotic tool holder, comprising:
a housing, configured to be gripped by a human hand;
a retaining cup at a distal end of the housing;
a wireless transmitter, located within the housing; and
a plurality of individual controls attached to the housing, each of the controls being configured for both a first mode and a second mode of operation, such that in the first mode of operation of the robotic tool holder, the controls are configured to activate respective motions of a first surgical tool physically attached to the housing, by insertion of the first surgical tool into the retaining cup, in response to manipulation of the controls by the human hand, and in the second mode of operation of the robotic tool holder, the controls are configured to activate via the wireless transmitter respective motions of a second surgical tool remote from and disconnected from the housing in response to the manipulation.

2. The holder according to claim 1, wherein the individual controls comprise a magnification/demagnification regulator having a setting defining a ratio, so that in the first mode of operation the ratio corresponds to a movement of a given control relative to a corresponding movement of the first surgical tool and in the second mode of operation the ratio corresponds to the movement of the given control relative to a corresponding movement of the second surgical tool.

3. The holder according to claim 1, wherein the controls comprise a flexible joint attached to the housing, wherein the retaining cup is attached to the flexible joint, the flexible joint being configured so that in the first mode of operation a movement of the housing with respect to the flexible joint generates a corresponding movement of the first surgical tool with respect to the flexible joint.

4. The holder according to claim 1, and comprising a processing unit and motors mounted within the housing, wherein the processing unit receives signals from the plurality of individual controls, and in response:
in the first mode of operation operates the motors to activate the respective motions of the first surgical tool, and
in the second mode of operation causes the wireless transmitter to activate the respective motions of the second surgical tool.

5. The holder according to claim 1, and comprising a clamping system wherein is mounted the second surgical tool, and further comprising a processing unit external to the housing configured to receive signals from the wireless transmitter, and in response to operate the clamping system to perform the respective motions of the second surgical tool.

6. The holder according to claim 1, wherein the second surgical tool comprises a multiplicity of surgical tools remote from and disconnected from the housing, the controls comprising a selector configured to select in the second mode of operation a given surgical tool from the multiplicity of surgical tools.

7. The holder according to claim 1, wherein the robotic tool holder is operated in an operating theater, and wherein the controls comprise a selector configured to select a facility used in the operating theater.

8. A method for implementing a robotic tool holder, comprising:
configuring a housing to be gripped by a human hand;
locating a wireless transmitter within the housing; and
attaching a plurality of individual controls to the housing, wherein each of the controls is configured for both a first mode and a second mode of operation, such that in the first mode of operation of the robotic tool holder, the controls are configured to activate respective motions of a first surgical tool physically attached to the housing, by insertion of the first surgical tool into a retaining cup at a distal end of the housing, in response to manipulation of the controls by the human hand, and in the second mode of operation of the robotic tool holder, the controls are configured to activate via the wireless transmitter respective motions of a second surgical tool remote from and disconnected from the housing in response to the manipulation.

9. The method according to claim 8, wherein the individual controls comprise a magnification/demagnification regulator having a setting defining a ratio, so that in the first mode of operation the ratio corresponds to a movement of a given control relative to a corresponding movement of the first surgical tool and in the second mode of operation the ratio corresponds to the movement of the given control relative to a corresponding movement of the second surgical tool.

10. The method according to claim 8, wherein the controls comprise a flexible joint attached to the housing, wherein the retaining cup is attached to the flexible joint, the flexible joint being configured so that in the first mode of operation a movement of the housing with respect to the flexible joint generates a corresponding movement of the first surgical tool with respect to the flexible joint.

11. The method according to claim 8, and comprising mounting a processing unit and motors within the housing, wherein the processing unit receives signals from the plurality of individual controls, and in response:
in the first mode of operation operates the motors to activate the respective motions of the first surgical tool, and
in the second mode of operation causes the wireless transmitter to activate the respective motions of the second surgical tool.

12. The method according to claim 8, and comprising a mounting the second surgical tool with a clamping system, and further comprising configuring a processing unit external to the housing to receive signals from the wireless transmitter, and in response to operate the clamping system to perform the respective motions of the second surgical tool.

13. The method according to claim 8, wherein the second surgical tool comprises a multiplicity of surgical tools remote from and disconnected from the housing, the controls comprising a selector configured to select in the second mode of operation a given surgical tool from the multiplicity of surgical tools.

14. The method according to claim 8, and comprising operating the robotic tool holder in an operating theater, and wherein the controls comprise a selector configured to select a facility used in the operating theater.

* * * * *